Aug. 13, 1974 A. BARBERET ET AL Plant Pat. 3,591
CARNATION PLANT
Filed March 30, 1973
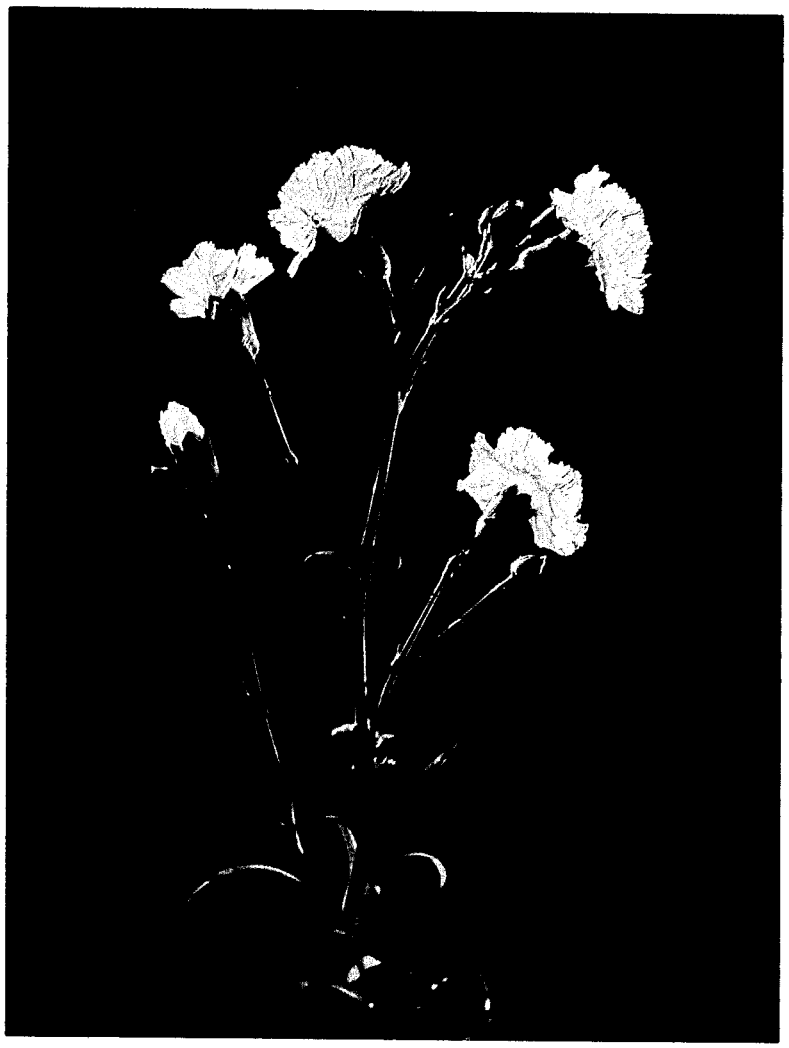

United States Patent Office

Plant Pat. 3,591

Patented Aug. 13, 1974

3,591

CARNATION PLANT

Alexandre Barberet and Henri Blanc, La Londe, France, assignors to Laboratoire de Physiologie Vegetale de la Londe Barberet & Blanc, La Londe, France

Filed Mar. 30, 1973, Ser. No. 346,716

Claims priority, application Italy, Dec. 22, 1972, 33,460/72

Int. Cl. A01h *5/00*

U.S. Cl. Plt.—70 1 Claim

ABSTRACT OF THE DISCLOSURE

A new variety of carnation plant of the miniature type distinguished by the pale pink color of its blossoms, the good branched arrangement of the inflorescense, its continuous high production of flowers on short sturdy stems, and its vigorous habit of growth.

BACKGROUND OF THE NEW PLANT

This new variety of carnation plant originated as a seedling selected in 1969 from among a number of plants resulting from a crossing made under our direction at La Londe, France, between two unnamed varieties forming part of our collection which is maintained for the purpose of producing improved carnation plants for the commercial market. This plant was selected because of its high production of well formed flowers on relatively short, rigid stems branching from a strong main stem that is substantially self supporting; and because of the very unusual soft pink overall coloring of the inflorescense. Asexual propagation of this new variety under our direction by cuttings and through many generations at La Londe, France, has shown the distinctive growth and color characteristics of the plant to be firmly fixed and to hold true, in all respects, from generation to generation.

DESCRIPTION OF THE DRAWING

Our new variety of pink carnation plant is illustrated by the accompanying photographically produced drawing which shows the color characteristics of the new plant as nearly true as it is reasonably possible to obtain through conventional photographic procedures, the view showing the branching habit of the new plant as well as buds and various stages of inflorescense opening.

DESCRIPTION OF THE NEW PLANT

The following is a detailed description of this new variety of carnation plant based upon observations made in December 1972, at La Londe, France, on greenhouse plants set out in May 1972. The color designations are according to the R.H.S. Horticultural Colour Chart issued by The Royal Horticultural Society at London, England.

*The plant*

Origin: Seedling.

Parentage:

*Seed Parent.*—191V—unnamed and unpatented.

*Pollen Parent.*—7VII—unnamed and unpatented. These parent plants are growing under glass at La Londe, France, and are identified in my permanent records by the above stated numbers.

Classification:

*Botanic.*—Hybrid dianthus caryophyllus. Commercial—Spray carnation for cut flowers.

Form: Leafy bush.

Height: Full foliage to about 30 cm. for a six months old plant, flowering stems reaching an average maximum of about 60 cm.

Growth: Vigorous and erect with strong upright main stems having an average thickness of about 0.6 cm.

Branching: Upright and high with 5 to 8 primary flowering branches per main stem.

Foliage: Quantity—Abundant.

*Size of Leaf.*—Up to 11 cm. long and 1.2 cm. wide with the longest leaves appearing between the 6th and 12th main stem joints and the widest leaves at the 4th or 5th joints as counted from the base of the plant.

*Form of Leaf.*—Short, lanceolate, with acuminate apex and entire margins. Leaves extend upwardly from the stem and then either remain generally straight or curve downwardly. The leaves are rarely curled.

*Texture.*—Smooth.

*Color.*—Leaves—Upper and under sides—Greyed Green 189B. Nodes, joints—Yellow Green 145D. Main Stems—Between nodes—Greyed Green 189B. At the level of the nodes—Green 138D.

*Ribs.*—Single axial rib.

*Petioles.*—None; leaf is amplexicaul and decurrent.

Inflorescence, in General: Opening—Good. Same in winter.

*Branches.*—Principal branches—5 in number, 3 to 5 bearing secondary branching.

*Number of Flowers and Buds.*—9.

*The bud*

Calyx:

*Form.*—Rather globular at beginning, becoming ovoid before the sepals open and funnel-shaped when sepals unfurl.

*Size.*—Medium. Up to about 1.3 cm. in diameter and to 2.5 cm. in depth.

*Opening.*—Bud opens slowly.

*Sepals.*—Shape—Ovate and upstanding; 5 or 6 in number. Color: Inside—Pale Green; outside—Light Green.

*Aspect.*—Calyx has a smooth aspect and does not split.

Peduncles: Erect and rigid, forming an acute angle with the supporting stem. Average maximum length—18 cm.

*The flower*

Blooming Habit: Profuse and continuous, but late. The different levels of flowers open out one after the other from bottom to top without any precise order or regularity.

Size of Bloom: Medium.

*Diameter.*—Average 5.1 cm. Depth: About 2.3 cm.

Borne: Singly, in spray arrangement of floral stems.

Shape: Flat. Shape does not change as flower ages.

Petalage: About 32 in number, in more or less imbricated arrangement with 10 or 11 guard petals and center comprising two rows or circles of 8 to 12 petals in the first row and 10 to 12 petals in the second row often joined with the petaloids and stamens.

*Form of Petals.*—Fan shaped with rather smooth side margins and dentate apex.

*Color.*—The general color aspect of the blossoms is rose-violet which becomes lightened at full bloom. Fine violet stripes of variable length and density appear on the petals and violet teeth form a very fine edging or fringe on the apex margins of the petals.

The coloring of the blossom petals is as follows:

| | Upper side | Reverse side |
|---|---|---|
| Young flowers | Red Purple Group 65B–65C. | Red Purple Group 65D. |
| Mature flower | Red Purple 65D | Red Purple 62D. |
| Stripes | Red Purple 61A | Red Purple 71A. |

*Appearance.*—Satiny on the upper surface.
*Texture.*—Soft.

Petaloids: About 10 in number, half the size of petals.
*Color.*—Red Purple 65C.

Peduncle: Erect and rigid. Very short and green in color.

Discoloration: Color tends to lighten with flower age.

Effect of Weather: None.

Fragrance: Very faint; pleasant carnation odor.

Persistence: Petals hang on and dry.

Disease Resistance: Very good for the current diseases of carnations as observed at La Londe, France.

Lasting Quality: On plant—18 days in December. As cut flower—up to 15 days in December with stable ambient temperature of 23° C.

*Reproductive organs*

Stamens: Anthers—15 to 20, 3 mm. long and in random arrangement. Filaments—2.6 cm. long. Color: White. Pollen: Color—Yellowish.

Pistils: 2 in number—rarely 3. Length—2.5 cm.

Stigmas: Color—White and Violet.

Ovaries: Globulus and normal.

*Fruit*

The fruit is fertile and of oblong shape. Its color is green and ocherous.

The particular advantages found in this new variety of carnation plant reside in the unusual and very attractive coloring of its blossoms, its high branching and prolific production of flowers on short, rigid and strong stems. This plant has a vigorous growth habit, an abundant production of leaves which are sufficiently short to have little or no curling, and strong branching stems which often produce secondary flowering branches.

We claim:

1. A new and distinct variety of carnation plant, substantially as herein shown and described, characterized by the unique coloring of its blossoms, which are carried on short rigid stems, and by its vigorous and high branching growth habit which produces many flowers which mature more or less successively in a typical spray arrangement.

No references cited.

ROBERT E. BAGWILL, Primary Examiner